(12) United States Patent
Hartov et al.

(10) Patent No.: US 8,886,291 B2
(45) Date of Patent: Nov. 11, 2014

(54) SYSTEMS AND METHODS FOR COMBINED ULTRASOUND AND ELECTRICAL IMPEDANCE IMAGING

(75) Inventors: Alex Hartov, Enfield, NH (US); Keith D. Paulsen, Hanover, NH (US)

(73) Assignee: The Trustees of Dartmouth College, Hanover, NH (US)

(\*) Notice: Subject to any disclaimer, the term of this patent is extended or adjusted under 35 U.S.C. 154(b) by 843 days.

(21) Appl. No.: 12/812,407

(22) PCT Filed: Jan. 7, 2009

(86) PCT No.: PCT/US2009/030329
§ 371 (c)(1),
(2), (4) Date: Oct. 4, 2010

(87) PCT Pub. No.: WO2009/089280
PCT Pub. Date: Jul. 16, 2009

(65) Prior Publication Data
US 2011/0034806 A1 Feb. 10, 2011

Related U.S. Application Data

(60) Provisional application No. 61/020,042, filed on Jan. 9, 2008.

(51) Int. Cl.
| A61B 5/05 | (2006.01) |
| A61B 8/08 | (2006.01) |
| A61B 8/12 | (2006.01) |
| A61B 5/053 | (2006.01) |
| A61B 8/00 | (2006.01) |

(52) U.S. Cl.
CPC ............ *A61B 5/0536* (2013.01); *A61B 8/4472* (2013.01); *A61B 8/483* (2013.01); *A61B 8/12* (2013.01); *A61B 8/4411* (2013.01); *A61B 8/4416* (2013.01); *A61B 8/08* (2013.01)
USPC ............ 600/427; 600/442; 600/437; 382/128

(58) Field of Classification Search
None
See application file for complete search history.

(56) References Cited

U.S. PATENT DOCUMENTS

| 4,493,039 A | * | 1/1985 | Gregory .................. 324/228 |
| 6,291,180 B1 | | 9/2001 | Chu |
| 6,511,427 B1 | * | 1/2003 | Sliwa et al. ............. 600/438 |

(Continued)

OTHER PUBLICATIONS

Soleimani, Manuchehr, "Electrical Impedance Tomography Imaging Using a priori Ultrasound data," Biomedical Engineering Online, vol. 5, No. 1, pp. 1-8, Feb. 6, 2006.

(Continued)

*Primary Examiner* — Unsu Jung
*Assistant Examiner* — Michael N Fisher
(74) *Attorney, Agent, or Firm* — Lathrop & Gage LLP

(57) ABSTRACT

A dual imaging probe 300 for obtaining both ultrasound and electrical impedance data is disclosed along with methods of using the dual imaging probe 300 to interrogate tissue. An electrical impedance imaging overlay 330 is adapted to be positioned on a transducer window 304 of an ultrasound probe 320, and may be integrally formed as part of the ultrasound probe 320 or as a modular adapter for coupling with, and optionally uncoupling from, an ultrasound probe 320 to form the dual imaging probe 300. A method (FIG. 6) of reconstructing composite images using both ultrasound and electrical impedance data is described. Applications for medical diagnosis are described. A particular use for prostate imaging is described.

13 Claims, 4 Drawing Sheets

(56) References Cited

U.S. PATENT DOCUMENTS

| | | | |
|---|---|---|---|
| 2003/0028092 A1* | 2/2003 | Anderson et al. | 600/409 |
| 2003/0055478 A1* | 3/2003 | Lyster et al. | 607/142 |
| 2005/0101876 A1* | 5/2005 | Pearlman | 600/547 |
| 2006/0008128 A1* | 1/2006 | Setlak et al. | 382/124 |
| 2006/0030844 A1* | 2/2006 | Knight et al. | 606/41 |
| 2006/0074287 A1* | 4/2006 | Neumann et al. | 600/407 |
| 2006/0241514 A1* | 10/2006 | Davies | 600/547 |
| 2007/0014459 A1* | 1/2007 | Palmer | 382/128 |

OTHER PUBLICATIONS

International Search Report and Written Opinion issued in PCT/US2009/030329, dated Jun. 3, 2009, 18 pages.

* cited by examiner

SYSTEMS AND METHODS FOR COMBINED ULTRASOUND AND ELECTRICAL IMPEDANCE IMAGING

RELATED APPLICATION

The present application claims priority from U.S. Provisional Patent Application No. 61/020,042, filed 9 Jan. 2008, the disclosure of which is incorporated herein by reference.

U.S. GOVERNMENT RIGHTS

This invention was made with Government support under contract number 2 P01 CA080138-06A2 awarded by the National Institutes of Health. The U.S. Government has certain rights in this invention.

BACKGROUND

The prostate is a small gland that surrounds the urethra just anterior to the rectum. In men, especially elderly men, it often develops one or more of hypertrophy, benign cysts and nodules, and/or cancers. Prostate cancers range from slow growing, non-invasive types to highly aggressive, fast growing, and invasive types. As prognosis and treatment for each of these conditions differs, it is desirable to reliably distinguish them.

There are about 230,000 cases of prostate cancer diagnosed in the United States each year, but a large number of cases remain undetected. For example, studies show that needle biopsies miss 40-50% of clinically threatening carcinomas. This high occurrence of false negatives is troublesome because highly effective life-saving measures are available when detection occurs early in the disease.

To improve the odds of detection, several imaging modalities that guide biopsy procedures and/or provide independent diagnostic results have been developed. Transrectal ultrasound ("TRUS") is one such imaging technique that is typically used to guide biopsy needles. TRUS involves high frequency sound waves in the range of about 1 to 20 MHz. These sound waves are emitted by an ultrasound probe, then travel through tissue until they are reflected by interfaces between different types of tissues, such as between differing organs, between healthy tissue and denser cancerous tissue, or between soft tissue and bone. An ultrasound probe receives reflected sound waves (echoes) and instrumentation calculates distances between the probe and the reflecting boundary, typically displaying an image of detected boundaries. The ultrasound technique provides good (sub-millimeter) spatial resolution and can identify the borders of organs such as the prostate, and possibly can identify borders of tumors within such organs, but it is unable to discriminate between benign versus malignant tissue.

Electrical Impedance Imaging ("EII"), on the other hand, is a medical imaging technique that provides tissue characterization. The technique involves attaching conductive electrodes to a surface of a patient, applying small currents to two or more of the electrodes and measuring electrical potentials at one or more electrodes. From these measurements, electrical impedance of tissue may be determined. The process is repeated for many different configurations of the applied current. Subsequent computation produces a 3D map of the electrical properties of tissues, which correlate with tissue types and pathologies. EII offers low cost, low resolution, images limited by inaccurate modeling of regionally varying electrode-patient contact and poor signal-to-noise contrast.

SUMMARY

In an embodiment, an electrical impedance imaging (EII) electrode overlay is adapted to be positioned on a transducer of an ultrasound probe.

In an embodiment, a dual imaging probe includes an ultrasound probe and an Electrical Impedance Imaging (EII) electrode array having at least one electrode on an ultrasound transducer window of the ultrasound probe.

In an embodiment, a method for imaging tissue using a dual imaging probe includes: transmitting acoustic signals from a transducer through an Electrical Impedance Imaging (EII) overlay into a tissue, the EII overlay having multiple electrodes; receiving reflected acoustic signals; transducing the reflected acoustic signals into transduced electrical signals; sending the transduced electrical signals as ultrasound data to an electronic system; transmitting electrical current through a first subset of the electrodes of the EII overlay; measuring parameters including electrical current and/or electrical voltage at each electrode of a second subset of the electrodes of the EII overlay; sending the measured electrical parameters as EII data to the electronic system; and analyzing and co-registering the ultrasound data and the EII data to create at least one tomographic image of the tissue.

In another embodiment, a method for imaging tissue using a dual imaging probe includes: transmitting acoustic signals from a transducer of the probe; receiving reflected acoustic signals; transducing the reflected acoustic signals into transduced electrical signals; sending the transduced electrical signals as ultrasound data to an electronic system; transmitting electrical current through a first subset of a group of electrical impedance imaging (EII) electrodes of the probe; measuring electrical current and/or electrical voltage at each electrode of a second subset of the EII electrodes; sending the measured electrical parameters as EII data to the electronic system; and analyzing and co-registering the ultrasound data and the EII data to create at least one EII image of the tissue. In a particular embodiment the EII image is constructed by: extracting regions from the ultrasound data; constructing a finite element model of the tissue, the finite element model having an impedance parameter at each node of the model; constraining the model of the tissue with the regions extracted from the ultrasound data; and determining impedance at nodes of the model of the tissue such that simulation of the model of the tissue approximately matches measured EII data.

In an embodiment, a software product includes computer-readable instructions stored on computer-readable media. The instructions, when executed by a computer, perform steps for creating a tomographic image of a tissue. The software includes instructions for: transmitting acoustic signals from an ultrasound probe through an Electrical Impedance Imaging (EII) overlay into a tissue; receiving reflected acoustic signals; transducing the reflected acoustic signals into electrical signals; transmitting the electrical signals as ultrasound data to an electronic system; transmitting electrical current through a first electrode; measuring attenuation of the electrical current at a second electrode, the second electrode forming part of the EII overlay; transmitting the measured electrical current as EII data to the electronic system; and analyzing and co-registering the ultrasound data and the EII data to create one or more tomographic images of the tissue that may be used for diagnosis.

DETAILED DESCRIPTION

While ultrasound provides good resolution of tissue borders, and echogenicity of regions from tissue imperfections and density fluctuations gives some additional diagnostic information, ultrasound is not always sufficient for distinguishing normal and benign tissue types from malignant tissue types. Electrical Impedance Imaging ("EII") provides some information about tissue types, but has poor resolution.

The present instrumentalities relate to imaging systems and methods that combine ultrasound and EII. The combination of ultrasound and EII allows for improved identification of tissue borders and tissue types over EII alone, and better differentiation of normal, benign and malignant tissue types than available with ultrasound alone.

Figure 1:
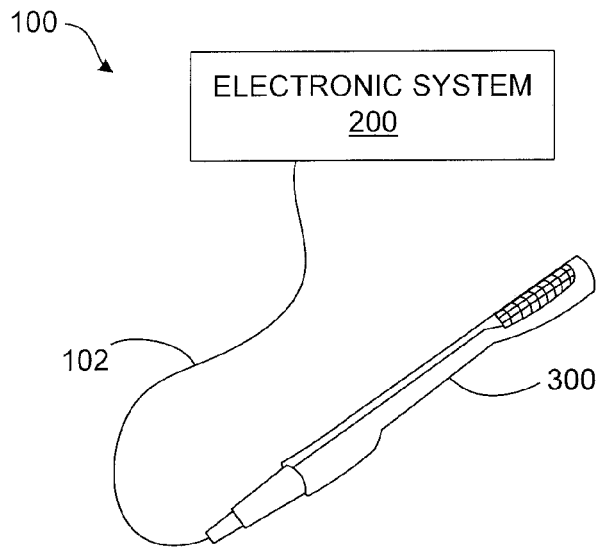
FIG. 1 shows an exemplary imaging system having an electronic system and a dual imaging probe, according to an embodiment.

FIG. 1 shows an exemplary imaging system 100, according to one embodiment. Imaging system 100 includes an electronic system 200 coupled to a dual imaging probe 300 via a connection 102. Electronic system 200 controls application of energy to dual imaging probe 300, which transmits electrical and/or ultrasound signals into tissue. Dual imaging probe 300 also collects electrical signals and/or reflected ultrasound signals and transfers data back to electronic system 200. Electronic system 200 may store and/or analyze the received data. Although connection 102 is shown in FIG. 1, it will be appreciated that dual imaging probe 300 may transfer collected data to electronic system 200 wirelessly when a probe battery, transmitter and receiver are included in system 100.

In one embodiment, dual imaging system 100 collects data using both ultrasound and EII sequentially, but within a brief time interval such that probe 300 does not move significantly between capture of ultrasound and EII data. The ultrasound and EII modalities are complementary because ultrasound provides good (sub-millimeter) spatial resolution while EII provides information on the state of the tissue albeit at a lower spatial resolution. For example, direct impedance measurements on ex vivo samples have shown that the resistivity of prostate tumors is often significantly greater than the resistivity of normal tissue; this greater resistivity permits EII to discriminate between tumor from normal tissue.

Figure 2:
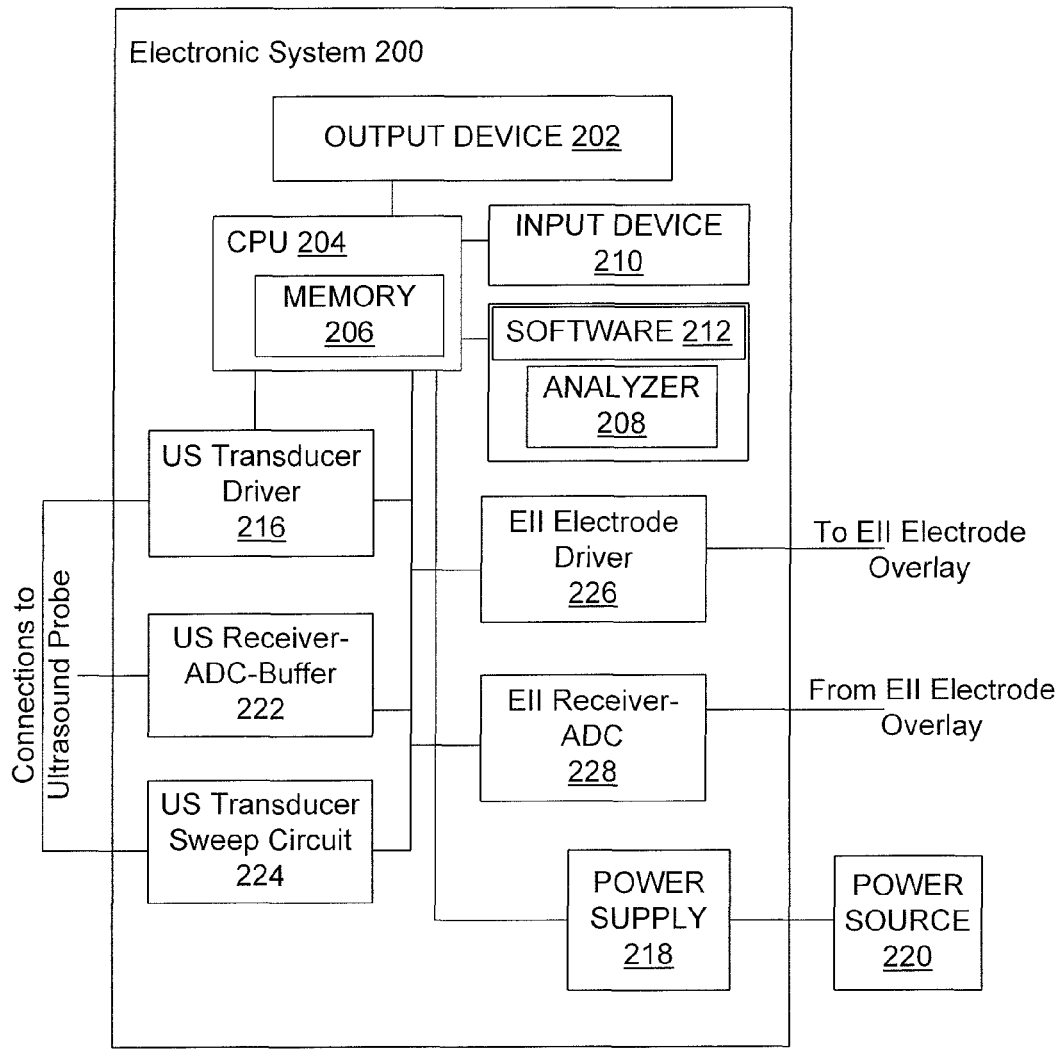
FIG. 2 shows an exemplary block diagram of the electronic system of FIG. 1.

FIG. 2 is an exemplary block diagram of electronic system 200, according to an embodiment. Electronic system 200 includes an output device 202, a central processing unit 204 (hereinafter, CPU 204) with associated memory 206 and software 212, an input device 210, and a power supply 218. Electronic system 200 receives power from a power source 220, which may for example be a standard 115-volt electrical outlet, in some countries a 240-volt outlet, or may be a battery. Power supply 218 converts power from power source 220 into a current and voltage usable by components of electronic system 200.

With reference to FIG. 2 and FIGS. 3, 4, and 5, ultrasound transducer driver 216 is provided for generating signals suitable for driving an ultrasound transducer within probe 300. The transducer typically has a phased array of piezoelectric ultrasonic transducer elements as known in the art of medical ultrasound, in other embodiments the transducer may have a unidirectional piezoelectric transducer mechanically scanned by a motor. The transducer is located below transducer window 304, and when driven by driver 216, emits pulses of ultrasonic sound waves through the transducer window 304 of the probe, through EII overlay 330, into tissue located near probe 300; at least some of these ultrasonic sound waves are typically reflected by nonuniformities in the tissue, these nonuniformities include boundaries between organs and differing tissue types, including boundaries between tumor and normal tissue, as well as dense materials such as bone.

A portion of the reflected sound waves are received through EII overlay 330 and transducer window 304, and are transduced to electrical signals by the ultrasound transducer of probe 300. The transducer window 304 is that portion of a housing of probe 300 that is adapted for emitting and receiving ultrasound from the transducer, while protecting the transducer's piezoelectric elements and associated circuitry from moisture present in the tissue, and is typically formed of electrically nonconductive plastic. The transduced electrical signals are processed by Ultrasound Receiver/Analog-Digital-Converter (ADC)/Buffer circuitry 222. The ultrasonic sound waves are typically formed into a beam that is repeatedly swept through an arc or volume of the tissue near probe 300 under control of transducer sweep circuit 224. CPU 204 uses data from US Receiver/ADC/Buffer 222 to construct an ultrasound representation in memory 206 of the tissue near probe 300, using techniques known in the art of ultrasound imaging; in many embodiments this ultrasound representation is a three-dimensional representation of the tissue. Images, which may be tomographic images, are derived from the ultrasound representation in memory. One or more of these images is typically displayed to an operator through output device 202 for verification of correct probe placement and preliminary diagnosis.

In an alternative embodiment, the EII overlay 330 is formed integral to the probe 300. In some embodiments, the nonconductive substrate of EII overlay 330 serves as transducer window 304. In some embodiments some or all of the EII overlay electrodes, such as electrodes 305, are located on portions of the ultrasound probe 300 other than the ultrasound window of the probe. As with embodiments having EII overlay electrodes on window 304, these electrodes are positioned to pass currents through portions of tissue that overlap a volume of tissue within an ultrasound field of view of the ultrasound probe.

In some embodiments, Ultrasound Receiver/ADC/Buffer circuitry 222 is capable of determining frequency shifts due to the Doppler effect, such as result when reflections arise from blood flowing in vessels within the tissue.

The Electrical Impedance Imaging (EII) electrode driver 226 provides alternating-current stimulus currents to at least a first subset of electrodes 314 of EII-imaging overlay 330. EII receiver-ADC circuitry 228 is provided for monitoring voltages and currents at least a second subset of electrodes 314 of EII imaging overlay 330, this second subset of electrodes 314 may overlap the first subset. The first and second subsets of electrodes 314 may, but need not, overlap. In an embodiment, the stimulus currents have a predetermined frequency between 10 kHz and 10 MHz and currents low enough to avoid harm to the tissue.

In an embodiment, EII electrode driver 226 then provides alternating current stimulus currents to additional subsets of electrodes 314, while EII receiver-ADC circuitry 228, measures voltages and currents at additional subsets of electrodes 314, to provide additional EII measured data.

Signals from electronic system 200 are sent to dual imaging probe 300 along connection 102, and signals, including EII signals and transduced ultrasound signals, received by dual imaging probe 300 are likewise transmitted back to electronic system 200 along connection 102. CPU 204 includes a memory 206 for storing collected data, which may be in raw and/or processed form. Software 212 is executed by CPU 204. Software 212 includes instructions for analyzing collected data, using analyzer 208, spatially registering multiple sets of collected data and displaying one or more images on output device 202. A user may interact with electronic system 200 via input device 210 and output device 202.

Figure 3:
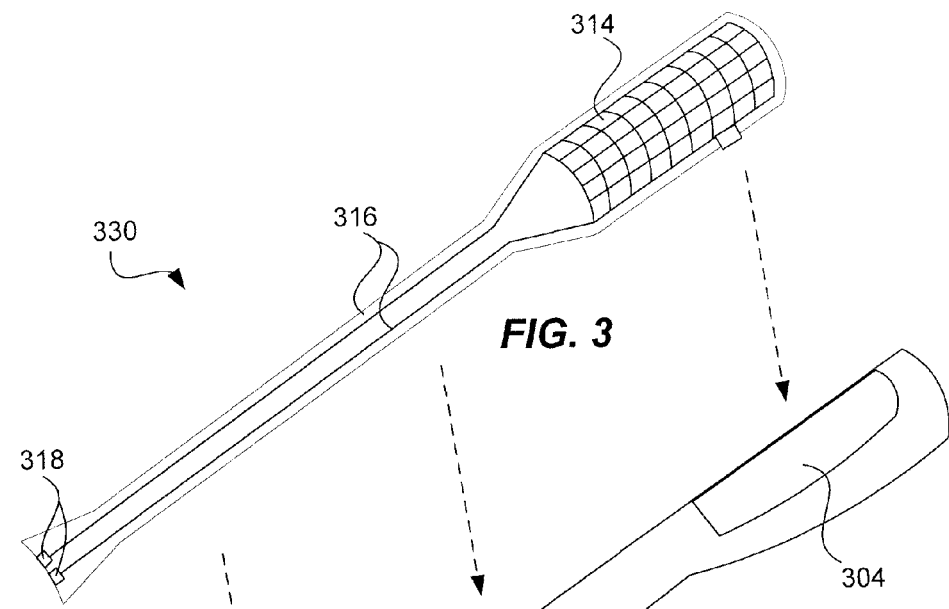
FIGS. 3, 4, and 5 show exemplary detail of the dual imaging probe of FIG. 1.
Figure 4:
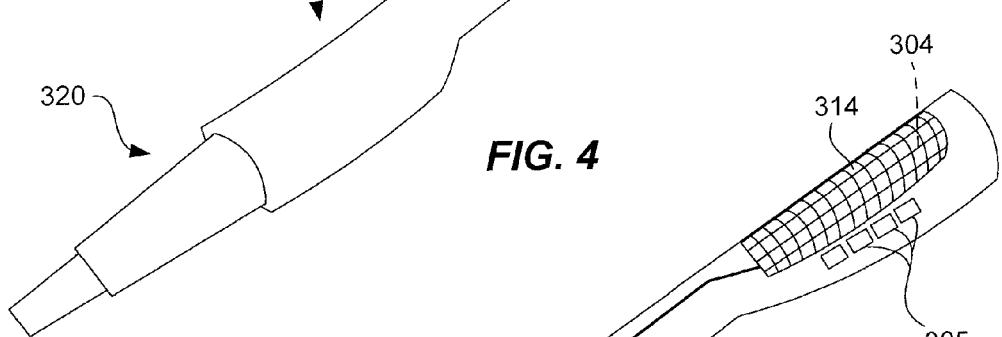
Figure 5:
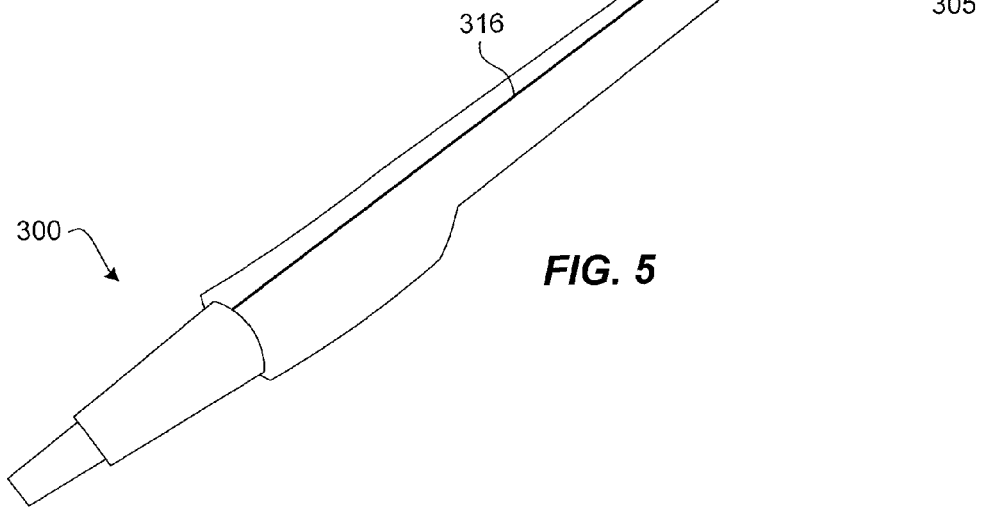

FIGS. 3, 4, and 5, when viewed together, show an exemplary dual imaging probe 300. Dual imaging probe 300 (FIG. 5) includes an ultrasound probe 320 (FIG. 4) and an electrical impedance imaging overlay 330 (FIG. 3). Typically, ultrasound probe 320 provides acoustic energy having a frequency of about 6-15 MHz for prostate imaging. For the interrogation of other tissues, higher frequencies may be used, e.g., 20-30 MHz. In one embodiment, EII overlay 330 may be integrally formed with ultrasound probe 320. In another embodiment, EII overlay 330 may be formed as a modular adapter capable of coupling with, and optionally uncoupling from, ultrasound probe 320. According to this later embodiment, EII overlay 330 may be used to retrofit an existing ultrasound probe. In either case, the presence of electrical components from EII overlay 330 on the surface of ultrasound probe 320 does not interfere with receipt or transmission of acoustic signals by the ultrasound probe. The positioning of EII overlay 330 on transducer window 304 advantageously allows for the use of a high density of electrodes 314 without loss of transducer surface area, and facilitates acquisition of a large number of data points, thereby providing good sensitivity.

EII overlay 330 may be a flexible electrical printed circuit formed, for example, as a grid of conductive metal electrodes 314 on a flexible nonconductive-plastic substrate such as those known in the art of printed circuits. The electrodes 314 couple through traces 316 to contacts 318, which couple with connection 102. The EII may have a nonconductive coating over traces 316 such that only electrodes 314 are permitted to electrically contact tissue. It will be appreciated that EII overlay 330 may include more than two traces 316 and may include switching devices that facilitate transfer of electrical current to and from predetermined subsets of electrodes 314. Electrodes 314 of EII overlay 330 form a contiguous surface such that a complete and consistent data set may be acquired. In one embodiment, the electrical components (e.g., electrodes 314, traces 316 and contacts 318) of EII overlay 330 may be printed, cast or otherwise fabricated with a flexible, dielectric polymeric material, such as polyethylene, polyfluoroethylene, polypropylene, polyethylene terephthalate, polyvinyl chloride, polystyrene and mixtures and copolymers thereof. It will be appreciated that although electrodes 314 must be in direct contact with tissue, traces 316 and contacts 318 are encapsulated within a dielectric polymeric material so that they are electrically insulated from tissue. It is desirable that the EII stimulus currents be limited to protect the patient. Electrodes 314 of EII overlay 330, which may be positioned over a transducer window 304 of ultrasound probe 320 and in a fixed spatial relation relative to the acoustic signals produced by ultrasound probe 320, may for example provide current of less than 10 mA at a frequency of about 10 KHz-10 MHz.

Calibration experiments, using standardized samples, may be performed to accommodate for spatial mismatch between the EII and ultrasound data. For example, by imaging objects in a water tank, it is possible to compute a calibration transformation matrix capable of merging the spaces defined in both frames of reference (e.g., ultrasound and EII). Various co-registration methods are described in the literature.

In an example of operation, software 212 includes instructions for automated acquisition of dual-modality data sets. For example, software 212 may provide instructions to collect and store data from EII overlay 330 and ultrasound probe 320 (simultaneously or sequentially). During or after data acquisition, software 212 may use a known co-registration method to merge the imaging spaces of ultrasound probe 320 and EII overlay 330. For example, since each imaging modality has its own coordinate system, software 212 may provide instructions to spatially transform or alter the spatial relationship between pixels of the images based on calibration data.

Dual imaging probe 300 may be used internally and/or externally in the detection and/or diagnosis of tumors, cysts, aneurisms, hematomas and plaques in tissue including, for example, breast, brain, prostate, ovarian, uterine, cervical, colon, ureter, urethral, heart, liver, esophageal, skin and pancreatic.

Figure 6:
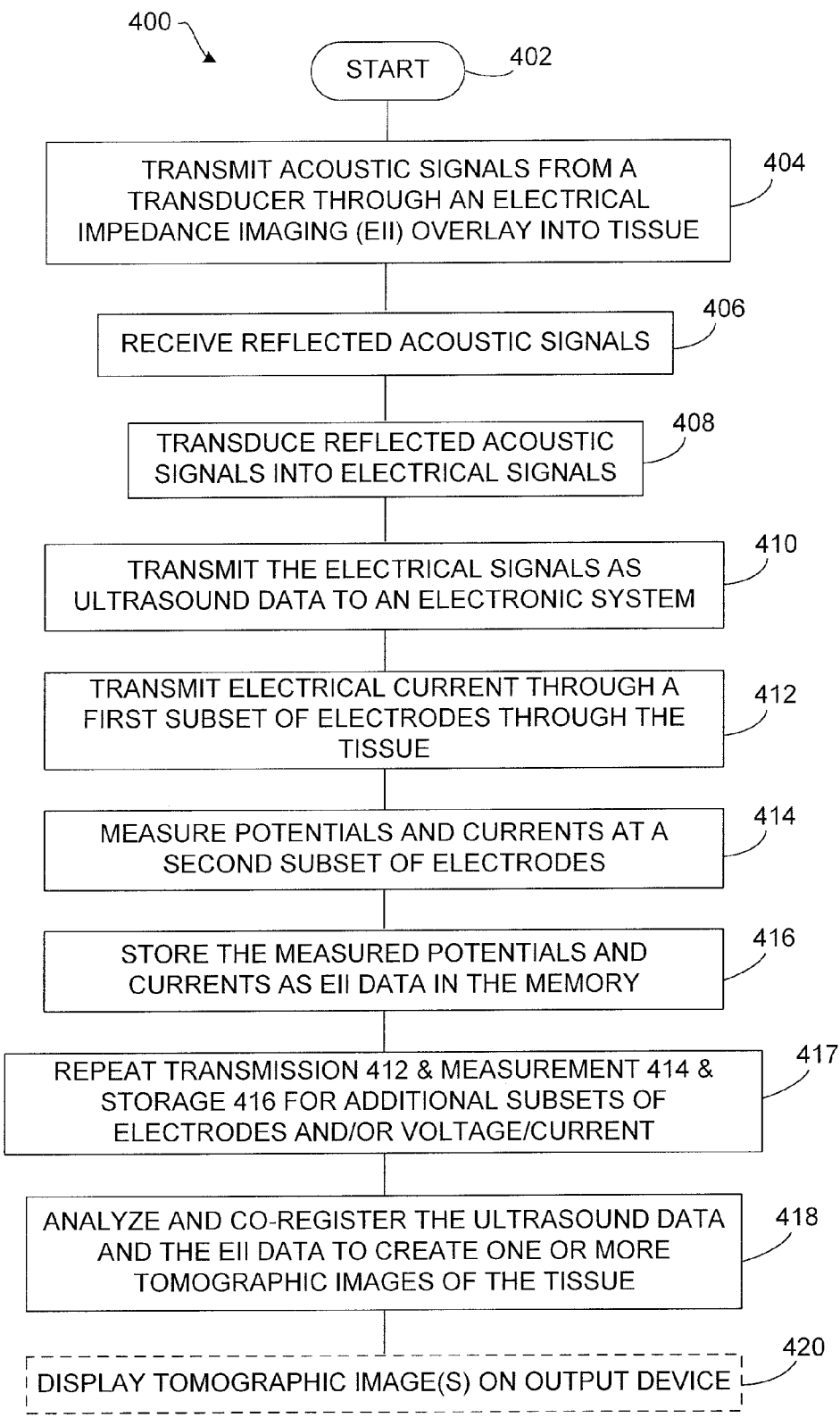
FIG. 6 is a flowchart illustrating a method for imaging tissue using a dual imaging probe, according to an embodiment.

FIG. 6 shows an exemplary method 400 for imaging tissue using a dual imaging probe (e.g., dual imaging probe 300). Method 400, in a prostate-imaging example, begins after a bowel preparation and insertion of the dual imaging probe into the rectum of a subject with the transducer window 304 of the dual imaging probe facing the prostate, during an initialization step 402. In step 404, a transducer, typically located behind transducer window 304 of the dual imaging probe, transmits ultrasound acoustic signals through the electrical impedance imaging (EII) overlay 330 through rectal mucosa into tissue of the prostate. Reflected acoustic signals (echoes) are received in step 406. In step 408, the reflected signals are transduced into electrical signals and, in step 410, the electrical signals are processed as ultrasound data by an electronic system (e.g., electronic system 200). The ultrasound data is preferably 3-D ultrasound data, which may be generated either by use of a 3-D probe or by use of a 2-D probe with probe-movement tracking apparatus.

In step 412, an electrical current from a first subset of electrodes, which may include electrodes 314 of EII overlay 330 and may include one or more additional electrodes, such as a perineal electrode and a ventral electrode, independent from dual imaging probe 300, is transmitted through the tissue. In step 414, resulting electrical potentials and currents are measured at selected electrodes (e.g., a second and potentially overlapping subset of electrodes 314) of the EII overlay. In step 416, the measured electrical voltages and currents are stored in memory 206 as EII measured data in the electronic system. In step 417, steps 412, 414, and 416 may be repeated for differing subsets of the electrodes and/or differing applied voltages and currents. The ultrasound data and the EII data are then analyzed and co-registered to create one or more electrical impedance three-dimensional tomographic images of the tissue in step 418.

Optionally, in step 420, various projections and slices of the ultrasound data and the electrical impedance tomographic image(s) may be displayed on an output device (e.g., output device 202). In one embodiment, the tomographic image(s) are three-dimensional images formed by the co-registration of 3-D ultrasound and 3-D electrical impedance maps. Alternatively, the images may be printed or saved electronically for later perusal by a physician.

When the present apparatus is used for imaging other body parts, such as the human breast, an electrically and ultrasonically conductive gel may be placed between skin or other body surface and the probe 300. The probe may have a shape varying from that illustrated in FIGS. 3, 4, and 5, as appropriate for the body part to be imaged. In particular, it is anticipated that a variety of topical, transesophageal and endoscopic probes may be fabricated in addition to transrectal probes for imaging various tissues.

Figure 7:
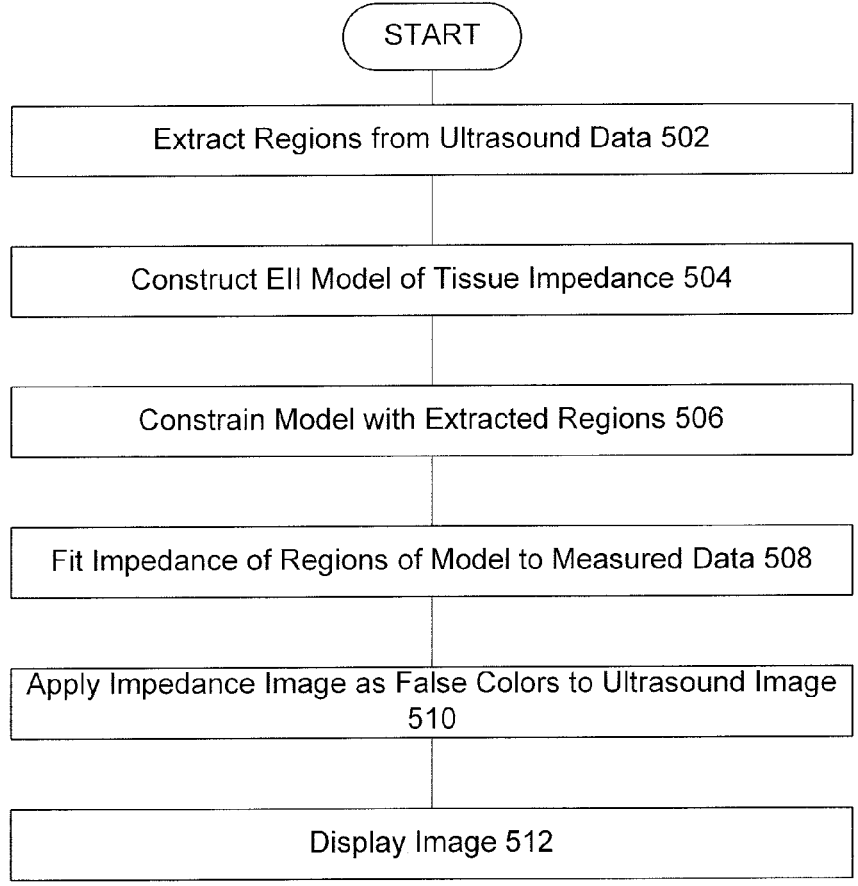
FIG. 7 is a detailed flowchart of step 418 in FIG. 4.

In an alternative embodiment, illustrated in FIG. 7, during step 418, after ultrasound and EII data are captured, regions of apparently similar tissue type are extracted from an ultrasound image 502. A finite element model of the currents in the tissue is created 504 with local tissue impedance as a variable at each node of the model. This model is a three-dimensional model and is initially constrained 506 to have similar impedance throughout regions of apparently similar tissue type according to the ultrasound data. Impedances of the regions of the model are then fitted 508 to the EII measured data, such that the local tissue impedance variables are adjusted until simulation of the model provides results that approximately match the measured EII data.

An image of a slice of the tissue having edges and regions extracted from the ultrasound data is then colored 510 using tissue impedance data from the refined three-dimensional model such that high impedance regions are red, mid-impedance regions are yellow, and low impedance regions are blue. The tissue-impedance data of each image corresponds to an intersection of a plane with the three dimensional model. The plane of the tissue-impedance data corresponds to the slice of the tissue imaged from the ultrasound data, so the resultant image represents coregistered ultrasound and electrical impedance data. Additional false-color images may be produced corresponding to other slices of the tissue. The false-color image or images are tomographic images in that each represents at least one slice of a three dimensional tissue.

The false-color image or images are then displayed 512, printed and/or saved for later viewing for diagnostic purposes. Typically, images of multiple slices are prepared so that a surgeon may study three-dimensional tumors or other structures as may occur in the tissue.

In addition to false-color composite images as described above, tomographic images derived from the ultrasound data and EII data may be separately displayed, saved and/or printed.

It will be appreciated that the above-described steps may be performed in an order that differs from what is explicitly described without departing from the scope of the present instrumentalities. It is also appreciated that different colors may be used than heretofore described with respect to false-color images.

For purposes of this document, a computer program product is a computer-readable memory device having recorded thereon or stored therein computer-executable instructions for performing a sequence of steps of a method. It is appreciated that the electronic system for co-registering and resolving the EII and ultrasound data incorporates one or more microprocessors or computers, at least one memory system for storing computer-executable instructions, and at least one memory system capable of storing EII and ultrasound data, tissue models, and generated images. The memory system for storing computer-executable instructions and the memory system capable of storing EII and ultrasound data may be the same memory system.

The changes described above, and others, may be made in the systems and methods described herein without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present methods and systems, which, as a matter of language, might be said to fall there between.

What is claimed is:

1. A method for imaging tissue using a dual imaging probe, comprising:
    transmitting acoustic signals from an ultrasound transducer through at least some metal electrodes of an array of electrodes into a tissue;
    receiving reflected acoustic signals through at least one electrode of the electrodes;
    transducing the reflected acoustic signals into transduced electrical signals;
    sending the transduced electrical signals as ultrasound data to an electronic system;
    transmitting electrical current through a first subset of the electrodes of an electrical impedance imaging (EII) overlay into a tissue, the EII overlay comprising a plurality of electrodes;
    measuring parameters selected from the group consisting of electrical current and electrical voltage at each electrode of a second subset of the electrodes of the EII overlay;
    sending the measured electrical parameters as EII data to the electronic system; and
    analyzing and co-registering the ultrasound data and the EII data to create at least one tomographic image of the tissue
    wherein the tomographic images are constructed by:
    extracting regions from the ultrasound data, the ultrasound data obtained simultaneously with the EII data and comprising images;
    constructing a finite element model of the tissue, the finite element model having impedance parameters at each node of the model;
    constraining the model with the regions extracted from the ultrasound data; and
    determining impedance at nodes of the model such that simulation of the model matches measured EII data.

2. The method of claim 1, further comprising displaying the at least one tomographic image on an output device.

3. The method of claim 1, further comprising evaluating the one or more tomographic images to make a diagnosis of damage or disease to the tissue.

4. The method of claim 1, wherein the acoustic signals have a frequency between 6 MHz and 30 MHz.

5. The method of claim 4, wherein the acoustic signals have a frequency between 6 MHz and 15 MHz.

6. The method of claim 4, wherein the electrical current is less than 10 mA.

7. The method of claim 6, wherein the one or more tomographic images are three-dimensional.

8. The method of claim 1, wherein a false-color image is constructed having edges extracted from the ultrasound data and colors representing impedance at nodes of the model corresponding to the regions extracted from the ultrasound data.

9. The method of claim 1, wherein at least one electrode of the EII overlay is located over an ultrasound imaging window of the probe.

10. A method for imaging tissue using a dual imaging probe, comprising:
    transmitting acoustic signals from a transducer of the probe through at least one metal electrode of a group of electrical impedance imaging (EII) electrodes of the probe;

receiving reflected acoustic signals through at least one electrode of a group of electrical impedance imaging (EII) electrodes of the probe;

transducing the reflected acoustic signals into transduced electrical signals;

sending the transduced electrical signals as ultrasound data to an electronic system;

transmitting electrical current through a first subset of the group of electrical impedance imaging (EII) electrodes of the probe;

measuring parameters selected from the group consisting of electrical current and electrical voltage at each electrode of a second subset of the EII electrodes;

sending the measured electrical parameters as EII data to the electronic system; and analyzing and co-registering the ultrasound data and the EII data to create at least one EII image of the tissue; wherein the EII image is constructed by:

extracting regions from the ultrasound data;

constructing a finite element model of the tissue, the finite element model having an impedance parameter at each node of the model;

constraining the model of the tissue with the regions extracted from the ultrasound data; and determining impedance at nodes of the model of the tissue such that simulation of the model of the tissue matches measured EII data.

11. The method of claim 10 wherein the tissue comprises a prostate gland.

12. A computer program product for constructing images of tissue comprising a machine readable memory device having stored therein computer readable instructions for:

reading ultrasound data, the ultrasound data acquired by transmitting acoustic signals from a transducer through at least one metal electrode of at least a first subset of electrodes into tissue, receiving reflected acoustic signals, transducing the reflected acoustic signals into transduced electrical signals, and recording the transduced electrical signals as ultrasound data in an electronic system;

reading electrical impedance imaging (EII) data, the EII data having been generated by transmitting electrical current through at least the first subset of electrodes, measuring parameters selected from the group consisting of electrical current and electrical voltage at each electrode of at least a second subset of electrodes of an EII overlay, and recording the measured electrical current and voltage as EII data; and analyzing and co-registering the ultrasound data and the EII data to create at least one composite tomographic image of the tissue by:

extracting regions from the ultrasound data, the ultrasound data comprising images;

constructing a finite element model of the tissue, the finite element model having impedance parameters at each node of the model;

constraining the model with boundaries corresponding to regions extracted from the ultrasound data; and determining impedance at nodes of the model such that simulation of the model matches measured EII data.

13. A combined electrical impedance imaging (EII) and ultrasound imaging probe for imaging tissue comprising:

an ultrasound imaging probe having at least one ultrasound transducer window configured such that, when the probe is driven by an ultrasound driver, sound waves are emitted from the ultrasound transducer window;

an EII overlay further comprising a plurality of electrodes for electrically contacting tissue, the overlay disposed on the ultrasound imaging probe with at least some of the electrodes of the overlay over the ultrasound transducer window of the probe such that sound waves emitted from the ultrasound transducer window pass through a metal electrode of the EII overlay into the tissue;

an apparatus adapted to obtain EII data through the EII overlay;

an ultrasound imaging system adapted to obtain ultrasound image data through the ultrasound imaging probe; and a processor configured with machine readable instructions adapted to extract regions from the ultrasound image data, the ultrasound data obtained simultaneously with the EII data;

construct a finite element model of the tissue, the finite element model having impedance parameters at each node of the model; and constrain the model with the regions extracted from the ultrasound data; and determine impedance at nodes of the model such that simulation of the model matches measured EII data.

* * * * *